United States Patent [19]

Soma et al.

[11] Patent Number: 4,544,640

[45] Date of Patent: Oct. 1, 1985

[54] ANTI IMMUNE COMPLEX ANTIBODY FOR DETERMINING SLE, RHEUMATOID ARTHRITIS OR TETANUS

[75] Inventors: Kazunori Soma; Yasushi Kasahara, both of Tokyo, Japan

[73] Assignee: Fujizoki Pharmaceutical Co., Ltd., Tokyo, Japan

[21] Appl. No.: 482,766

[22] Filed: Apr. 7, 1983

[30] Foreign Application Priority Data

Apr. 9, 1982 [JP] Japan ................................. 57-58274
Nov. 29, 1982 [JP] Japan ................................. 57-207658

[51] Int. Cl.$^4$ ............................................. G01N 33/54
[52] U.S. Cl. ................................. 436/506; 260/112 R; 435/7; 435/68; 435/172.2; 436/507; 436/509; 436/512; 436/547; 436/548; 935/93; 935/110
[58] Field of Search ............... 436/506, 507, 509, 512, 436/547, 548; 260/112 R; 435/172.2

[56] References Cited

U.S. PATENT DOCUMENTS

| 4,210,622 | 7/1980 | Soothill | 436/506 X |
| 4,283,383 | 8/1981 | Masson | 436/509 X |
| 4,332,783 | 6/1982 | Pernice | 436/506 |
| 4,342,566 | 8/1982 | Theofilopoulos | 436/507 |

OTHER PUBLICATIONS

Chemical Abstracts, 88: 168279p (1978).

Primary Examiner—Sidney Marantz
Attorney, Agent, or Firm—Burgess, Ryan & Wayne

[57] ABSTRACT

An antibody is obtained by using as an antigen a complex of an antigen and the F(ab')$_2$ fragment of the human antibody of this antigen or an aggregate of the F(ab')$_2$ fragment of human immunoglobulin. This antibody reacts with an immune complex in a blood serum of a patient of systemic lupus erythematosus and with an immune complex in a blood serum of a patient of rheumatoid arthritis, and it does not react with an aggregated IgG. The amount of immune complex in a blood serum is easily and exactly determined by using this antibody.

22 Claims, No Drawings

ANTI IMMUNE COMPLEX ANTIBODY FOR DETERMINING SLE, RHEUMATOID ARTHRITIS OR TETANUS

This invention related to a novel antibody capable of detecting an immune complex and relates to its preparation method and use.

Immune complex is the combined product of an antigen, an antibody and a complement. When this immune complex is formed in a human body, the immune complex is usually rendered harmless by a leucocyte or a macrophage. However, when a large quantity of antigen exists in a human body, or when an antigen the antibody of which forms with difficulty, exists in a human body, the amount of immune complex increases, and it causes various diseases such as acute glomerulonephritis, angitis, chronic urticaria, and thrombocytopenia.

Various measuring methods of this immune complex are known such as the method utilizing a reaction of complement or rheumatoid factor with the immune complex, the method utilizing a reaction of the Fc receptor with the immune complex, and various physicochemical methods such as the gel filtration method, the sucrose density gradient centrifuge and precipitation with polyethyleneglycol. However, the method using the complement or rheumatoid factor and the method using Fc receptor have a fatal defect in that these methods cannot distinguish between aggregated IgG and the immune complex. The physicochemical methods are complicated and they are insufficient in specificity.

Recently, a new method using an anti-antibody which recognizes a structural change of the Fab fragment caused by the combination of antigen and antibody was reported by Kano et al. (K. Kano et al., Clinical Immunology and Immunopathology, vol. 9, pp 425–435 (1978). This method utilizes the inhibition of the immune complex in a sample blood serum which inhibits agglutination between anti-antibody having 3 agglutinating units and anti D antibody sensitized blood cell. The procedure of this method is simple, and this method specifically detects the immune complex, and does not detect the aggregated IgG. However, this anti-antibody is not easily obtained.

The present inventors have found that when a complex of an antigen and the F(ab')2 fragment of the human antibody of this antigen is injected into a warm-blooded animal other than a human to form a novel antibody in the body of the animal, this novel antibody specifically detects the immune complex, and it can detect various immune complexes. They further found that this antibody can also be produced by injecting an aggregate of the F(ab')2 fragment of human immunoglobulin as an antigen into a warm-blooded animal other than a human such as a rabbit. They still further found that it can also be produced as a monoclonal antibody.

Properties of the anti immune complex antibody of the invention which was obtained in Example 1 are as follows:

(1) Reactions with immune complexes, aggregated human IgG, etc.

This antibody reacts with the immune complexes in the blood sera of patients with systemic lupus erythematosus and chronic articular rheumatism and the immune complex of inactivated tetanus toxoid and anti tetanus toxoid human IgG. On the other hand, this antibody does not react with aggregated IgG obtained by heating and IgG obtained from its immune complex. The above measurements were carried out according to the ELISA method which is described in Example 4.

The reactivities between the antibody of the invention and the complex of tetanus toxoid and anti tetanus toxoid human IgG, tetanus toxoid, anti tetanus toxoid human IgG, human IgG, aggregated human IgG, human F(ab')2 fragment, and aggregated human F(ab')2 fragment were measured by the Ouchterlony immunodiffusion method. Precipitation lines appeared between this antibody and the above complex and between this antibody and the aggregated human F(ab')2 fragment, whereas a precipitation line did not appear between this antibody and other substances.

(2) Molecular weight
Obtained from a rabbit and guinea pig blood sera:
150,000–160,000 (gel filtration)
150,000 9SDS polyacrylamide electrophoresis)
Obtained from chicken blood serum:
160,000–180,000 (gel filtration)

(3) Sedimentation coefficient
Obtained from a rabbit and guinea pig blood sera:
6.5 (Meniscus depletion method)
Obtained from chicken blood serum:
7.1 (Meniscus depletion method)

(4) Content of saccharides
Obtained from a rabbit and guinea pig blood sera:
2–4% (Phenol-sulfuric acid method)
Obtained from chicken blood serum:
3.5–4.5% (Phenol-Sulfuric acid method)

(5) Isoelectric point
Obtained from a rabbit and guinea pig blood serum:
5.8–8.7

Since the foregoing complex of an antigen and the F(ab')2 fragment or the aggregate of the F(ab')2 fragment of human immunoglobulin has never been injected into any living body, the present antibody is clearly novel. When this antibody is compared with the anti-antibody employed in the Kano's method, since this antibody is obtained from a warm-blooded animal other than a human while the anti-antibody was obtained from a human body, this antibody is fundamentally different from the antibody.

The present antibody may be prepared by using the complex of an antigen and the F(ab)2 fragment of the human antibody of this antigen or by using the aggregate of the F(ab')2 fragment of human immunoglobulin as its antigen.

When the present antibody is prepared by using the complex of an antigen and the F(ab')2 fragment of the human antibody of this antigen, the kind of the antigen is not limited. However, it is preferable that the antigen is water-soluble. The antigen includes horse IgG and human thyroglobulin derived from the thyroid gland and tetanus toxoid. The antigen may preferably be purified prior to use.

The antiboby which is the raw material of the F(ab')2 fragment corresponds to the above antigen, and it is human antibody. Among various antibodies such as IgG antibody, IgM antibody and IgE antibody, IgG antibody is preferable. The antibody can be obtained from human blood by any conventional method such as Cohn's method, the rivanol precipitation method, the polyethylene glycol method, and the gel filtration method, prior to use.

The F(ab')2 fragment may be prepared according to any conventional method, and usually, the antibody is digested with pepsin. The F(ab')$_2$ fragment may preferably be separated from the digest and purified. The separation may preferably be carried out according to known fractionation methods such as gel filtration, since molecular weight of the F(ab')$_2$ fragment does not depend on the kind of raw antibody and it is almost about 100,000.

The complex of the antigen and the F(ab')$_2$ fragment is produced by mixing in a solution. The pH of the solution is preferably kept at 5 to 9, and a buffer solution is usually employed. The preferable concentration of the antigen is 1.0 to 10 mg/ml, and that of the F(ab')$_2$ fragment is 1.0 to 10 mg/ml. The preferable molar ratio of the antigen/the F(ab')$_2$ fragment is about 3. The complex formed is stabilized by NaCl, and accordingly, NaCl is preferably added to the solution. In order to form the complex completely, the mixed solution is preferably warmed at 35° to 40° C. for 1 to 6 hours.

The complex formed is separated by gel filtration and lyophilized, if necessary.

The complex thus obtained is a glycoprotein of which the saccharide content determined by the phenolsulfuric acid method is about 2 to 6%. It molecular weight determined by the gel filtration method is about 300,000 to 500,000, and its sedimentation coefficient determined by the meniscus depletion method is about 10.8 to 15.2.

When the present antibody is prepared by using the aggregate of the F(ab')$_2$ fragment of human immunoglobulin, the kind of the human immunoglobulin is not limited. However, IgG is the most preferable. The immunoglobulin is purified by the conventional method, if necessary. The F(ab')$_2$ fragment is prepared and purified by the same method as previously described.

The F(ab')$_2$ fragment is aggregated by heating, acid treatment, treatment with guanidine hydrochloride, or treatment with urea. When the F(ab')2 fragment is aggregated, the F(ab')$_2$ fragment is first dissolved in a saline solution or a bufer and saline solution in a concentration of 1 to 30 mg/ml. And, in the case of heating, the solution is heated at 55° to 70° C. for 5 to 30 minutes. In the case of acid treatment, the solution is adjusted to pH 1.5 to 3 by using hydrochloric acid, and allowed to stand for 1 to 18 hours. In the case of treatment with guanidine hydrochloride, guanidine hydrochloride is added in a concentration of 5 to 8M to the solution of which pH is previously adjusted to 6.0 to 8.0 by using buffer solution, and the mixed solution is allowed to stand for 5 minutes to 18 hours.

The aggregate formed is purified by gel filtration and lyophilized, if necessary.

The antibiody of the invention may be prepared in vivo and in vitro.

In the former case, various warm-blooded animals, such as rabbit, guinea pig and chicken may be employed. In order to increase the yield of the antibody, endowment of immunotolerance to the warm-blooded animal is preferable. In the case of a rabbit weighing 3 kg, when 10 mg of F(ab')$_2$ fragment is injected, the immunotolerance appears after 1 to 3 days. In the case of other animals, the injection amount is determined on the basis of the ratio of its body weight/body weight of the rabbit (3 kg).

The complex of the antigen and the F(ab')$_2$ fragment or the aggregate of the F(ab')$_2$ fragment is injected into the warm-blooded animal. Injections are made several times at an interval of 2 days to 2 weeks. The injection amount per each time is, in the case of rabbit, 0.1 to 5 mg. In the case of guinea pig, the amount is 0.05 to 3 mg, and in the case of chicken, it is 0.1 to 10 mg.

When the antibody is produced as a monoclonal antibody, 50 to 200 μg of the above complex or the above aggregate is injected into the abdominal cavity of a BALB/C strain mouse, and its spleen is isolated after two weeks. The spleen cell is fused with mouse myeloma P301 cell by a conventional method such as by using polyethylene glycol. The hybridoma thus obtained is cultured and cloned and the cell capable of producing the antibody of the invention is obtained. This cell is injected into the abdominal cavity of a mouse, and multiplied. Then, ascites are collected and the antibody of the invention is separated from the ascites.

The antibody thus produced is separated from blood by a conventional method of separating immunoglobulin such as precipitation using ammonium sulfate, ion-exchange chromatography using DEAE-cellulose and the gel filtration method. Cohn's method, the rivanol precipitation method, and the polyethylene glycol method are also applicable. The antibody is further purified by affinity chromatography using Sepharose coupled with the same F(ab')$_2$ fragment as employed in the process to produce this antibody, and thereby antibodies capable of reacting with this F(ab')$_2$ fragment are removed.

On the other hand, when the antibody is separated from ascites, the separation is carried out only by salting-out with ammonium sulfate and gel filtration or by affinity chromatography using the carrier coupled with an anti mouse IgG antibody, and affinity chromatography using the Sepharose coupled with the F(ab')$_2$ fragment is not necessary.

Since the antibody of the invention specifically reacts with immune complex and does not react with aggregated IgG, this antibody can be substituted for the anti-antibody employed in Kano's method. This Kano's method has not been put to practical use, because it uses the anti-antibody which is produced by using a human body. However, the present antibody can be produced by using an animal other than human, and it can also be produced as a monoclonal antibody. Both the complex of an antigen and the F(ab')$_2$ fragment and the aggregate of the F(ab')$_2$ fragment of human immunoglobulin can easily be obtained from waste blood.

The present antibody widely reacts with various immune complexes and these immune complexes can be detected by using only one antibody. The present invention makes the detection of immune complex practical and helps the treatment of various diseases caused by immune complex.

The use of the present antibody is not limited to the substitution of the anti-antibody of the Kano's method, and the antibody may be used for the detection of immune complex by enzyme immunoassay.

EXAMPLE 1

Blood containing anti horse serum antibody obtained from a healthy person infected with tetanus and given anti tetanus horse serum was employed. According to the conventional manner, blood serum was separated from the blood and purified by salting-out using ammonium sulfate. Then, the precipitate was fractionated by ion exchange chromatography using DEAE cellulose and the IgG fraction was obtained. This fraction was purified by affinity chromatography using Sepharose 4B (manufactured by Pharmacia AB) coupled with horse IgG, and anti horse IgG human IgG was obtained.

1000 mg of this human IgG was dissolved in 200 ml of 0.01M borate buffer solution of pH 4.5. 10 mg of pepsin was added to the solution, and kept at 37° C. for 18 hours to produce the F(ab')$_2$. This pepsin digest was separated by gel filtration using Sephadex G-200 (manufactured by Pharmacia AB). Absorbance at 280 nm of the effluent of the Sephadex G-200 column was measured and the second peak fractions of the absorbance was collected. The collected fractions which contained the F(ab')$_2$ fragment were then lyophilized.

200 mg of this F(ab')$_2$ fragment and 600 mg of horse IgG were dissolved in 30 ml of 0.001M tris-HCl buffer solution of pH 8.0 and the solution was slowly stirred at 37° for 2 hours. This solution was then applied to a Sephacryl S-300 (manufactured by Pharmacia AB) column, and the first peak fraction (absorbance at 280 nm) was collected. The first peak fraction was lyophilized to obtain the lyophilized matter of a complex of horse IgG and the anti horse IgG human F(ab')$_2$ fragment.

On the other hand, the previously prepared F(ab')$_2$ fragment was dissolved in a saline solution and 10 mg of the fragment per one rabbit was injected to 20 rabbits into their ear veins. These 20 rabbits were bled for 2 days, and they were admitted as an immunotolerance group.

The above lyophilized matter of the complex was dissolved in a saline solution in a concentration of 4 mg/ml and an equal amount of Freund complete adjuvant was added to the solution. The mixture was emulsified and used as the antigen. 0.5 ml of this emulsion per one time and one rabbit was injected three times to 20 rabbits of the immunotolerance group and 20 rabbits of an untreated group every two weeks. After a week from the third injection, whole blood of each rabbit was drawn from its carotid.

Blood serum of each rabbit was separated individually and 12.15 g of ammonium sulfate (40% saturation) was added to each 50 ml of the blood serum. The blood serum was then stirrred for 30 minutes individually, and the precipitate was collected by centrifuging at 8000 rpm for 30 minutes. The precipitate was dialyzed overnight against pH 8.0 of 0.01M tris-HCl buffer solution 30 l, the dialysate was applied to the column (2.0 cm×60 cm) of DE-52 (made by Whatman Separation Ltd.) which was previously equilibrated with pH 8.0 of 0.02M tris-HCl buffer solution. The fractions passing through the column were dialyzed overnight against 30 of 0.01M borate buffer solution of pH 8.5, and the dialysate was applied to the column (1.6 cm×10 cm) of Sepharose 4B (manufactured by Pharmacia AB) coupled with horse IgG which was previously equilibrated with pH 8.5 of 0.1M borate buffer solution. The fraction passing through this column was collected and this fraction was applied to the column (1.6 cm×10 cm) of Sepharose 4B (manufactured by Pharmacia AB) coupled with anti horse IgG human F(ab')$_2$ fragment which was previously equilibrated with pH 8.5 of 0.1M borate buffer solution. The fraction passing through this column was collected and dialyzed overnight against a 20 l saline solution containing pH 8.0 of 1/1000M tris-HCl buffer solution. The dialysate was lyophilized and 10 mg of the lyophilized matter per one rabbit was obtained.

The reaction of each lyophilized matter with a serum of a patient having systemic lupus erythematosus which indicated positive with respect to immune complex by the $C_{lq}$ method was examined by the ouchterlony method using an agar plate and from the lyophilized materials of 3 rabbits among the untreated group and those of 5 rabbits among the immunotolerance group were found a precipitation line.

The columns used in this Example were prepared as follows:

8 g of Sepharose 4B which was activated by CNBr was put on a glass filter and washed with 1400 ml of 1 mM HCl. Then, it was put into a beaker and 500 mg of horse IgG (or anti horse IgG human F(ab')$_2$ fragment) which was dissolved in 100 ml of 0.1M NaHCO$_3$ buffer solution of pH 9.0 containing 0.5M NaCl was added to the Sepharose 4B. The mixture was kept at room temperature for two hours with occasional stirring and then filtered. Subsequently, 150 ml of 0.1M tris-HCl buffer solution of pH 8.0 was added to this Sepharose 4B and the mixture was kept at room temperature for two hours with occasional stirring and filtered. The Sepharose 4B coupled with the horse IgG (or the anti horse IgG human F(ab')$_2$ fragment) on the filter was washed three times with 150 ml of 0.1M borate buffer solution of pH 8.0, and then twice with 150 ml of 0.1M acetate buffer solution of pH 4.0. The washed Sepharose 4B was packed in a column and equilibrated with pH 8.5 of 0.1M borate buffer solution and used for the purification.

Using the positive lyophilized matter obtained in this Example, an immune complex test was carried out according to Kano's method. Namely, this lyophilized matter was dissolved in pH 7.2 of 0.15M phosphate buffer solution containing 0.14M NaCl in a concentration of 10 ug/ml and each 20 ul of this solution was mixed with each 20 ul of sample serum which was previously diluted with each dilution ratio. The mixture was kept at 20° C. for 60 minutes and put in a well of a micro titer plate. Then, 20 ul of 1% anti D antibody sensitized human blood cell belonging to group O Rh positive was added to each well and kept at 20° C. for 30 minutes in a humidified room and then judged. When the sample serum diluted 4 times still inhibits the agglutination of the sensitized blood cell, the sample serum was judged as positive.

The results are tabulated in the following table. In the table, SLE represents blood serum of a patient of systemic lupus erythematosus and RA represents blood serum of a patient of rheumatoid arthritis. RA was previously treated with 0.2M 2-mercaptoethanol and used for the test. "Addition" means that the sample serum was heated at 50° C. for 30 minutes.

|  | Number of Samples | Percentage of Positive | Percentage of Positive after Addition |
|---|---|---|---|
| SLE | 20 | 40% | 40% |
| RA | 21 | 71 | 71 |
| Healthy Persons | 18 | 0 | 0 |

Though heat-aggregated IgG was added to half the number of the sera of healthy persons in a concentration of 200 μg per 1 ml of the serum, none indicates positive.

EXAMPLE 2

The same F(ab')$_2$ fragment as employed in Example 1 was dissolved in a saline solution and 5 mg of the fragment per one guinea pig was injected to 30 guinea pigs into their volar veins. These 30 guinea pigs were bled for 3 days, and they were admitted as an immunotolerance group. 0.5 ml of the same emulsion as employed in example 1 per one time and one guinea pig was administered four times by intracutaneous injection to 30 guinea pigs of the immunotolerance group and 25 guinea pigs of an untreated group every two weeks. After a week from the last injection, whole blood of each guinea pig was drawn from its carotid.

Each 5 ml of blood serum of each guinea pig was separated individually and treated according to the same manner as employed in Example 1 to obtain 0.9 mg of the lyophilized matter per one guinea pig.

The reaction of each lyophilized matter with a serum of a patient of systemic lupus erythematosus which indicated positive with respect to immune complex was examiner according to the same manner as Example 1 and the lyophilized materials of 3 guinea pigs among the untreated group and those of 6 guinea pigs among the immunotolerance group were found to be positive.

EXAMPLE 3

The same F(ab')$_2$ fragment as Example 1 was dissolved in a saline solution and 10 mg of the fragment per one chicken was injected in 18 chickens into their veins. These 18 chickens were bled for a week and they were admitted as an immunotolerance group. 0.5 ml of the same emulsion as Example 1 per one time and one chicken was administered three times by intramuscular injection in the chests of 18 chickens of the immunotolerance group and those of 17 chickens of an untreated group every week. After a week from the last injection, whole blood of each chicken was drawn from its carotid.

Each 70 ml of blood serum of each chicken was separated individually and treated according to the same manner as Example 1 to obtain 9 mg of the lyophilized material per one chicken.

The reaction of each lyophilized material with a serum of a patient of systemic lupus erythematosus which indicated positive with respect to immune complex was examined according to the same manner as Example 1, and the lyophilized material of 2 chickens among the untreated group and those of 5 chickens among the immunotolerance group were found to be positive.

EXAMPLE 4

Blood serum separated from preserved human blood was treated by salting-out using ammonium sulfate and fractionated by ion exchange chromatography using DEAE cellulose to obtain IgG fraction.

1000 mg of this IgG was dissolved in 200 ml of 0.01M borate buffer solution of pH 4.3. 10 mg of pepsin was added to this solution and stirred at 37° C. for 18 hours. This pepsin digest solution was separated by gel filtration using Sephadex G-200 (manufactured by Pharmacia AB). Absorbance at 280 nm of effluent of the Sephadex G-200 column was measured and the second peak fractions of the absorbance was collected. The collected fractions were treated with Sepharose 4B (manufactured by Pharmacia AB) coupled with protein A to remove unreacted IgG and Fc fragment. The fractions passing through the column were collected and lyophilized to obtain 500 mg of the F(ab')$_2$ fragment.

50 mg of the F(ab')$_2$ fragment was dissolved in a saline solution in a concentration of 10 mg/ml and heated at 65° C. for 5 minutes and rapidly cooled, immediately. The heat treated solution was lyophilized and the lyophilized material was used as an antigen.

1 ml of the saline solution of the unheated F(ab')$_2$ fragment described above per one rabbit was injected in 10 rabbits having a body weight of 3 kg, in their ear veins. The above-mentioned antigen was dissolved in a saline solution in a concentration of 4 mg/ml and an equal amount of Freund complete adjuvant was added to the solution and the mixture was emulsified. After 3 days, 0.5 ml of this emulsion per one time and one rabbit was injected three times in the 10 rabbits every two weeks into their front leg and hind leg of intracutaneous and thigh muscle. After a week from the third injection, whole blood was drawn from their carotids.

500 ml of blood serum was separated from the blood and 121 g of ammonium sulfate was added to the serum. The serum was stirred for 30 minutes and the precipitate was collected by centrifuging at 8000 rpm for 30 minutes. This precipitate was dialyzed overnight against 100 l of 0.02M tris-HCl buffer solution of pH 8.0 and the residue was passed through a column (1.5 cm × 80 cm) of DE-52 (made by Whatman Separation Ltd.) which was previously equilibrated with pH 8.0 of 0.02M tris-HCl buffer solution. The fractions passing through the column were dialyzed overnight against 100 l of 0.01M borate buffer solution of pH 8.5 and the dialysate was applied to a column (2.0 cm × 20 cm) of Sepharose 4B (manufactured by Pharmacia AB) coupled with the unheated F(ab')$_2$ fragment described above which was previously equilibrated with pH 8.5 of 0.1M borate buffer solution. The fractions passing through the column were collected and dialyzed overnight against a saline solution containing pH 8.0 of 1/1000M tris-HCl buffer solution. The dialysate was lyophilized and 500 mg of the lyophilized material of the antibody of the invention was obtained.

Using the lyophilized material of the antibody, an immune complex test was carried out according to the ELISA method. Namely, the lyophilized antibody was dissolved in pH 7.2 of 0.02M phosphate buffer solution in a concentration of 60 μg/ml, and 60 μl of this solution was put in each well of a plate having 96 wells for the ELISA test. Then, the solution in the well was allowed to stand at 4° C. overnight, and the antibody in the solution was adsorbed on the surface of the well. Each well was washed, and 60 μl of 0.02M phosphate buffer solution containing 1% bovine serum albumin was put in each well. Ten ml of a human blood serum diluted 5 times with a saline solution was added to each well and reacted at room temperature for 2 hours. After the reaction, the solution in the well was drawn out and the wells were washed. Peroxidase conjugated anti human IgG goat antibody 50 ml was put in each well and reacted for 2 hours. After washing, 50 μl of peroxidase substrate of $H_2O_2$-2,2'-azino-di-[3-ethyl-benziazolin sulfate] was added to each well and reacted for 30 minutes at room temperature. After the reaction, absorbances of the reaction mixtures at 405 nm were measured.

As a result, in the case of the sera of the healthy persons, $OD_{405} = 0.02$ (n=20), in the case of the sera of the systemic lupus erythematosus patients, $OD_{405} = 1.8 - 0.5$ (n=40) and in the case of the sera of the chronic rheumatoid arthritis patients, $OD_{405} = 2.0 - 1.2$ (n=21). When 100 μg of heat-aggregated human IgG per 1 ml of the serum of a healthy person was added, the $OD_{405}$ value of the serum was also 0.02

EXAMPLE 5

The antigen obtained in the same manner as employed in Example 4 was dissolved in a saline solution in a concentration of 1000 μg/ml and 0.1 ml of this solution was injected into the abdominal cavity of a BALB/C mouse of 8 weeks growth. After a week, the injection was repeated again in the same manner. After another week and still another week, 50 μg/0.1 ml of a saline solution of the antigen was injected into its tail vein and 3 days later, its spleen was isolated. This spleen was ground and spleen cell was separated. The spleen cell was fused with mouse myeloma P3U1 cell by using polyethylene glycol 1500. The hybridoma was put in each well of a plate having 96 wells and cultured in the HAT medium. The cell of each well was examined by the ELISA method; the cells of 6 wells were positive. The positive cell means that it reacts with an aggregated human F(ab')$_2$ fragment and it does not react with a human F(ab')$_2$ fragment which is not aggregated. These positive cells were diluted by the limit dilution method and cloned and 7 positive cell lines were obtained.

Each positive cell line was multiplied in the 10% FCS-RPMI medium, each $10^7$ of the multiplied cells were injected into the abdominal cavity of a BALB/C mouse (previously injected pristane (Aldrich) 0.5 ml). After two weeks, about 10 ml of ascites was withdrawn. The ascites were treated by the precipitation method using ammonium sulfate in 45% saturation and dialyzed against 10 l of 0.02M tris-HCl buffer solution of pH 8.0. The dialysate was applied to a column of Sephadex G-200 (manufactured by Pharmacia AB) which was previously equilibrated with pH 7.0 of 0.1M phosphate buffer solution and the fractions corresponding to a molecular weight of 150000 to 200000 were collected. Absorbance of the collected fractions at 280 nm was measured and it was determined that these fractions contained 5 to 12 mg of IgG.

These fractions were reacted with the immune complex separated from the serum of a SLE patient by means of the ELISA method and the fractions obtained 3 cell lines were reacted.

Using these reactive fractions and the sera of healthy persons, the SLE patients and the RA patients, the immune complex test was carried out according to the ELISA method; the same absorbances as in Example 4 were obtained.

EXAMPLE 6

The human F(ab')$_2$ fragment prepared according to the same manner as Example 4 was dissolved in a saline solution in a concentration of 10 mg/ml and the pH of the solution was adjusted to 2.0 by using 0.1N HCl. This solution was allowed to stand at 4° C. for 18 hours.

The acid treated solution was neutralized with 0.1N NaOH and an equal amount of Freund complete adjuvant was added to the solution. The mixture was emulsified and 0.5 ml (containing 0.1 mg of the antigen) of this emulsion per one time and one guinea pig was administered 4 times by intracutaneous injection in the backs of 30 guinea pigs which were previously given immunotolerance every two weeks. After a week from the last injection, whole blood was drawn from their carotids.

This blood was treated in the same manner as in Example 4; 40 mg of the lyophilized material of anti immune complex antibody was obtained.

EXAMPLE 7

The human F(ab')$_2$ fragment prepared in the same manner as Example 4 was dissolved in pH 8.0 of 0.02M phosphate buffer solution in a concentration of 10 mg/ml and guanidine HCl was added to the solution in a concentration of 8M. This solution was allowed to stand at room temperature for 3 hours and dialyzed against a saline solution.

The residue was mixed with an equal volume of Freund complete adjuvant and emulsified. 0.5 ml of this emulsion per one time and one chicken was administered 3 times by intramuscular injection in the chests of 18 chickens which were previously given immunotolerance every two weeks. After a week from the last injection, whole blood was drawn from their carotids.

The blood was treated by the same manner as Example 4, and 160 mg of the lyophilized matter of anti immune complex antibody was obtained.

What is claimed is:

1. An anti-immune complex antibody, which is a glycoprotein having a molecular weight of from 150,000 to 180,000, as determined by gel filtration, reacts with an immune complex in a blood serum of a human patient having systemic lupus erythematosus, rheumatoid arthritis or tetanus, and which does not react with aggregated IgG.

2. An anti-immune complex antibody as claimed in claim 1, in the form of a monoclonal antibody.

3. An anti-immune complex antibody as claimed in claim 1, which is the antibody to a complex of an antigen and the F(ab')$_2$ fragment of the human antibody to said antigen, and derived from a warm-blooded animal other than a human.

4. An anti-immune complex antibody, as claimed in claim 3, in the form of a monoclonal antibody.

5. An anti-immune complex antibody, as claimed in claim 3, wherein said antigen is water-soluble.

6. An anti-immune complex antibody as claimed in claim 1, which is the antibody to an aggregate of the F(ab')$_2$ fragment of human immunoglobulin, and derived from a warm-blooded animal other than a human.

7. An anti-immune complex antibody, as claimed in claim 6, in the form of a monoclonal antibody.

8. An anti-immune complex antibody, as claimed in claim 6, wherein said antigen is water-soluble.

9. An anti-immune complex antibody, as claimed in claim 6, wherein said human immunoglobulin is IgG.

10. A method of producing the anti-immune complex antibody of claim 1, which comprises producing a complex of an antigen and a F(ab')$_2$ fragment of the human antibody of this antigen, producing an antibody by using said complex as an antigen, and recovering said last-mentioned antibody as said anti-immune complex antibody.

11. A method of producing an anti-immune complex antibody as claimed in claim 10, wherein said complex is produced by contacting said antigen and said F(ab')$_2$ fragment of the human antibody of this antigen in solution.

12. A method of producing an anti-immune complex antibody as claimed in claim 11, wherein said antibody is derived from a warm-blooded animal other than a human by using said complex as an antigen.

13. A method of producing an anti-immune complex antibody as claimed in claim 12, wherein said antibody is produced in vitro.

14. A method of producing an anti-immune complex antibody as claimed in claim 12, wherein said antibody is produced in vivo.

15. A method of producing an anti-immune complex antibody as claimed in claim 12, wherein said warm-blooded animal is selected from the group consisting of rabbits, guinea pigs, and chickens.

16. A method of producing the anti-immune complex antibody of claim 1, which comprises producing said antibody by using an aggregate of the F(ab')$_2$ fragment of human immunoglobulin as an antigen, and recovering said antibody.

17. A method of producing an anti-immune complex antibody as claimed in claim 16, wherein said antibody is derived from a warm-blooded animal other than a human by using said complex as an antigen.

18. A method of producing an anti-immune complex antibody as claimed in claim 17, wherein said antibody is produced in vitro.

19. A method of producing an anti-immune complex antibody as claimed in claim 17, wherein said antibody is produced in vivo.

20. A method of producing an anti-immune complex antibody as claim in claim 17, wherein said warm-blooded animal is selected from the group consisting of rabbits, guinea pigs, and chickens.

21. A method of producing an anti-immune complex antibody as claimed in claim 16, wherein said human immunoglobulin is IgG.

22. A method of determining an immune complex in the blood serum of a patient with systemic lupus erythematosus, chronic articular rheumatism, or tetanus toxoid, comprising contacting the respective antibody of claim 1 with said blood serum to thereby react the immune complex with said antibody.

* * * * *